United States Patent
Fischer et al.

(10) Patent No.: US 9,440,986 B2
(45) Date of Patent: *Sep. 13, 2016

(54) CRYSTALLINE, ANHYDROUS FORMS OF OXYMORPHONE HYDROCHLORIDE

(71) Applicant: ENDO PHARMACEUTICALS INC., Malvern, PA (US)

(72) Inventors: Andreas Fischer, Hürtgenwald (DE); Dagmar Peters-Groth, Aachen (DE); Dagmar Lischke, Inden-Altdorf (DE)

(73) Assignee: ENDO PHARMACEUTICALS INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/613,421

(22) Filed: Feb. 4, 2015

(65) Prior Publication Data

US 2015/0148368 A1    May 28, 2015

Related U.S. Application Data

(63) Continuation of application No. 14/091,399, filed on Nov. 27, 2013, now Pat. No. 8,969,368, which is a continuation of application No. PCT/EP2012/059705, filed on May 24, 2012.

(60) Provisional application No. 61/490,705, filed on May 27, 2011.

(51) Int. Cl.
*A61K 31/485* (2006.01)
*C07D 489/08* (2006.01)

(52) U.S. Cl.
CPC ......... *C07D 489/08* (2013.01); *C07B 2200/13* (2013.01)

(58) Field of Classification Search
USPC .............................................. 514/282; 546/45
See application file for complete search history.

(56) References Cited

U.S. PATENT DOCUMENTS

| | | | |
|---|---|---|---|
| 8,563,571 B2 | 10/2013 | Gushurst et al. | |
| 8,969,368 B2 * | 3/2015 | Fischer et al. | 514/282 |
| 2008/0146601 A1 | 6/2008 | Dung et al. | |
| 2010/0274019 A1 | 10/2010 | Huang | |
| 2011/0009634 A1 | 1/2011 | Huang | |
| 2012/0022093 A1 | 1/2012 | Gushurst et al. | |
| 2012/0156290 A1 | 6/2012 | Huang | |

FOREIGN PATENT DOCUMENTS

| | | |
|---|---|---|
| WO | 2008 048711 A1 | 4/2008 |
| WO | 2008 048957 A1 | 4/2008 |

OTHER PUBLICATIONS

Darling et al; "Operation of Long-Range Substituent Effects in Rigid Opiates: Protonated and Unprotonated Oxymorphone"; Journal of Pharmaceutical Sciences, vol. 71, No. 7, Jul. 1982, pp. 763-767.
Sime et al; "The Crystal Structure of a Narcotic Analgesic: Oxymorphone Hydrate"; Acta Cryst. 1973, pp. 2937-2940.

* cited by examiner

*Primary Examiner* — Charanjit Aulakh
(74) *Attorney, Agent, or Firm* — Mayer Brown LLP

(57) ABSTRACT

Crystalline, anhydrous hydrochloride salts of 4,5α-epoxy-3,14-dihydroxy-17-methylmorphinan-6-one (oxymorphone) are disclosed and three polymorphic forms of these salts are reported. The invention further relates to a method for the production of such salts, a pharmaceutical composition comprising an effective amount of such a salt and such a salt as a medicament and for the treatment and/or prevention of pain.

13 Claims, 4 Drawing Sheets

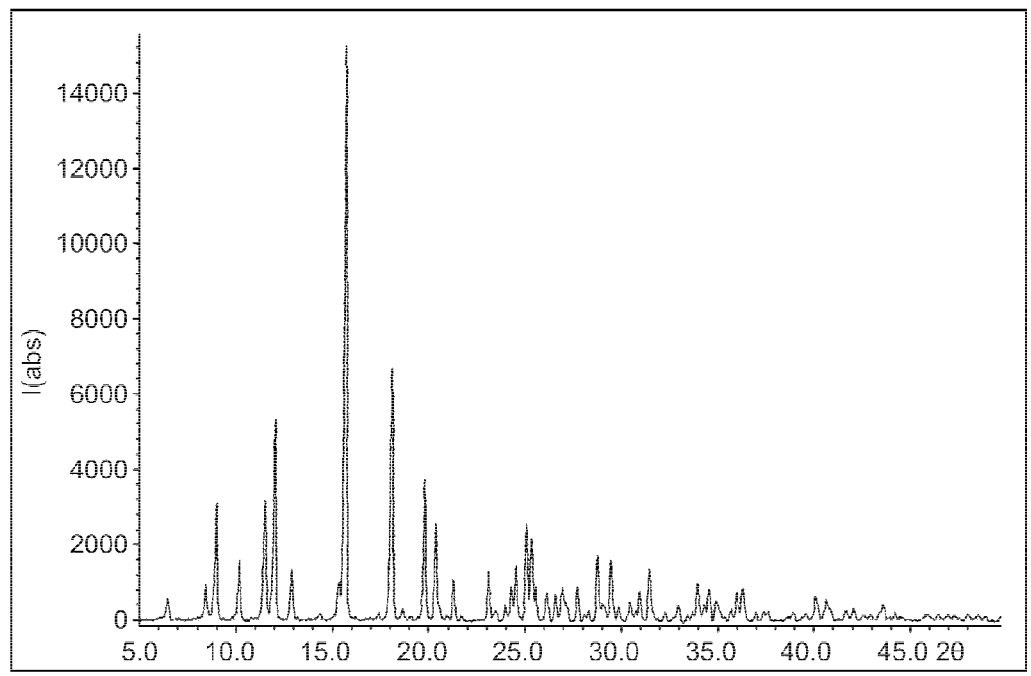
FIG. 1 (reference material)
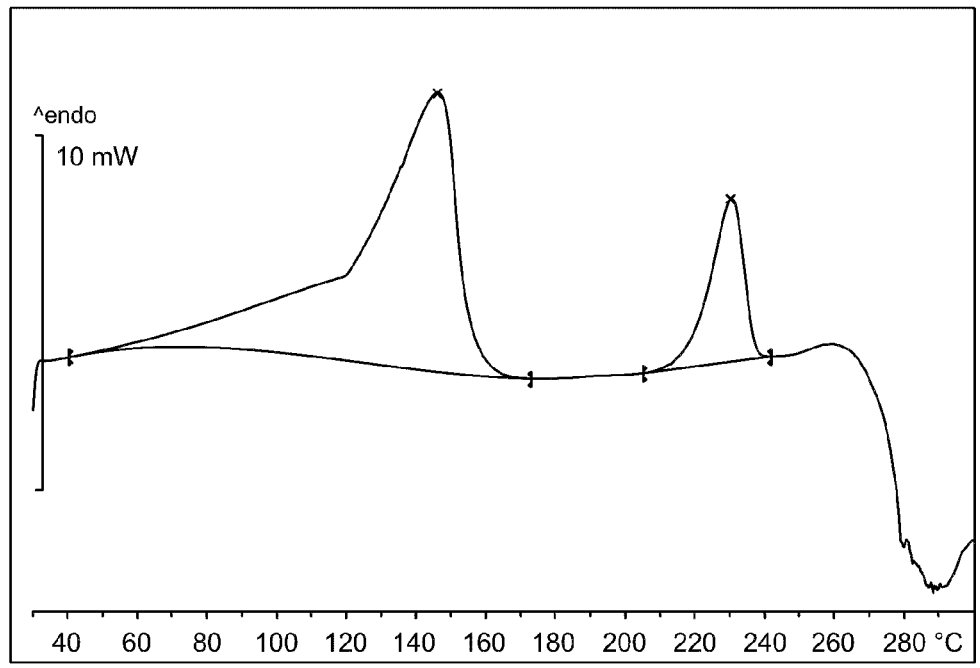
FIG. 2 (reference material)

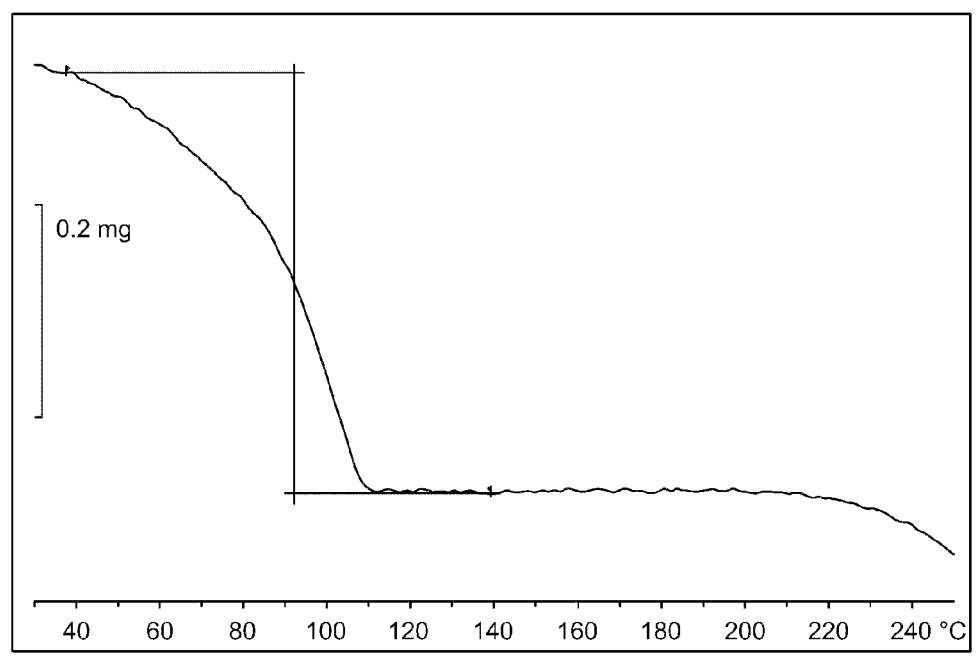
FIG. 3 (reference material)
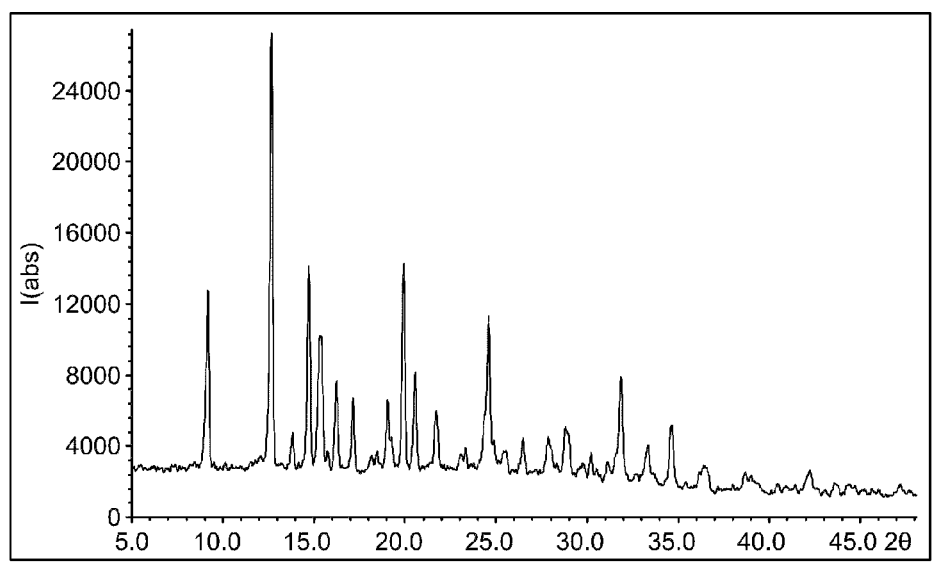
FIG. 4

CRYSTALLINE, ANHYDROUS FORMS OF OXYMORPHONE HYDROCHLORIDE

CROSS-REFERENCE TO RELATED APPLICATIONS

This application is a continuation of U.S. Non-provisional patent application Ser. No. 14/091,399, filed Nov. 27, 2013, now pending, which is a continuation of International Patent Application No. PCT/EP2012/059705, filed May 24, 2012, which claims priority benefit under 35 U.S.C. §119 of U.S. Provisional Patent Application No. 61/490,705, filed May 27, 2011, the disclosures of which patent applications are incorporated herein by reference.

The present invention relates to a crystalline, anhydrous hydrochloride salt of 4,5α-epoxy-3,14-dihydroxy-17-methylmorphinan-6-one (oxymorphone). The invention further relates to a method for the production of such a salt, a pharmaceutical composition comprising an effective amount of such a salt and such a salt as a medicament and for the treatment and/or prevention of pain.

Oxymorphone, generally administered in the form of its hydrochloride salt, is a potent semi-synthetic opiate analgesic, for the relief of moderate to severe pain, and has been approved for use in the United States since 1959. It can be administered as an injectable solution, suppository, tablet or extended release tablet. In general, it is commercially supplied as a monohydrate.

One of the more recent patent publications dealing with oxymorphone hydrochloride is US 2008/146601 A1 which discloses an improved analgesic oxymorphone hydrochloride that contains less than 10 ppm of alpha, beta unsaturated ketones and pharmaceutical preparations comprising such oxymorphone hydrochloride. The oxymorphone hydrochloride is produced by reducing a starting material oxymorphone hydrochloride using gaseous hydrogen and under specified acidity, solvent system and temperature conditions. A specific polymorph of oxymorphone hydrochloride may be obtained by hydration.

The crystal structure of the hydrochloride hydrate ethanol solvate is reported in S. D. Darling et al., J. Pharm. Sci. 1982, 71, 763 and the crystal structure of the free base hydrate in R. J. Sime et al., Acta Crystallographica Section B 1976, 32, 2937.

As a rule, the crystalline state of an active pharmaceutical substance has the advantage of an increased stability and processability.

A disadvantage of crystalline hydrates however is the possibility of solvent molecules also entering the crystal lattice. Furthermore, the microbiological contamination of hydrates may be accelerated when compared to substances lacking water.

It would therefore be desirable to have access to oxymorphone hydrochloride forms lacking these drawbacks. The present invention has the object of addressing these needs and of providing such oxymorphone hydrochloride salts.

According to the present invention this object is achieved by a crystalline, anhydrous hydrochloride salt of 4,5α-epoxy-3,14-dihydroxy-17-methylmorphinan-6-one according to formula (I):

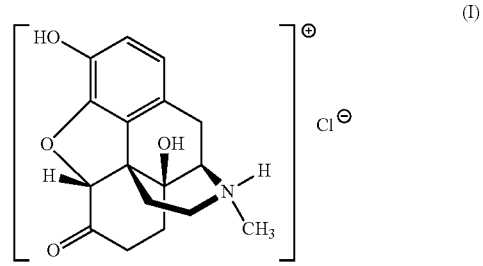

The compounds according to the invention are present in a crystalline state which is conveniently defined as the presence of one or preferably more reflexes in an X-ray powder diffractogram. In this respect the term "X-ray crystalline" is also used.

Besides avoiding the above-mentioned drawbacks in the art the anhydrous crystalline salts of the invention also have the advantage that no water content needs to be checked prior to employment in production and that no anisotropic water distribution within one storage vessel can occur.

In an embodiment of the hydrochloride salt according to the invention the melting or sublimation temperature, defined as the peak temperature in a differential scanning calorimetry measurement at a heating rate of 10° C./minute, is ≥250° C. Preferably, this temperature in a range of ≥280° C. to ≤290° C. and more preferred ≥285° C. to ≤286° C. The normalized integral of the melting enthalpy thus obtained is preferably in a range of ≥30 J/g to ≤40 J/g and more preferably ≥32 J/g to ≤34 J/g.

It has also been discovered that the crystalline, anhydrous oxymorphone salts of the present invention may be obtained in several polymorphic forms. Polymorphism, the occurrence of different crystal forms, is a property of some molecules and molecular complexes. A single molecule may give rise to a variety of polymorphs having distinct crystal structures and physical properties like melting point, x-ray diffraction pattern, infrared absorption fingerprint, and solid state NMR spectrum. One polymorph may give rise to thermal behavior different from that of another polymorph. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different polymorphs results from the orientation and intermolecular interactions of adjacent molecules or complexes in the bulk solid. Accordingly, polymorphs are distinct solids sharing the same molecular formula yet having distinct advantageous physical properties compared to other polymorphs of the same composition or complex.

The discovery of new polymorphic forms and solvates of a pharmaceutically useful composition provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Therefore, there is a need for additional polymorphs of oxymorphone hydrochloride.

Thus, in one particular embodiment of the hydrochloride salt according to the invention the X-ray powder diffractogram of the salt comprises one or more of the following reflexes (±0.2 in 2θ): 12.7, 14.7, 16.2, 17.1, 19.0. Preferably, the following reflexes (±0.2 in 2θ) are also included: 9.2, 13.8, 15.3, 19.9, 20.6, 21.7, 24.6, 31.9, 34.6.

In the context of the present invention this polymorph will be referred to as the "first polymorph". It is most preferred that its X-ray powder diffractogram comprises one or more of the following reflexes as stated in the following table 1 (±0.2 in 2θ and recorded using CuK$_\alpha$ radiation; the relative intensity I(rel) is 100 at most):

TABLE 1

| X-ray powder diffractogram | | | |
|---|---|---|---|
| 2θ | I(rel) | 2θ | I(rel) |
| 12.7 | 100 | 9.2 | 55 |
| 14.7 | 52 | 13.8 | 18 |
| 16.2 | 28 | 15.3 | 38 |
| 17.1 | 25 | 19.9 | 53 |
| 19.0 | 24 | 20.6 | 30 |
|  |  | 21.7 | 22 |
|  |  | 24.6 | 42 |
|  |  | 31.9 | 29 |
|  |  | 34.6 | 19 |

In another particular embodiment of the hydrochloride salt according to the invention the X-ray powder diffractogram of the salt comprises one or more of the following reflexes (±0.2 in 2θ): 6.0, 13.1, 13.6, 15.3, 16.5, 22.4, 22.6, 24.1. Preferably, the following reflexes (±0.2 in 2θ) are also included: 12.1, 29.8.

It is possible that the reflexes at 22.4 and 22.6 may not be resolved as a double peak if the sample quality is low. The case of these two peaks merging into one peak is also within the scope of the invention.

In the context of the present invention this polymorph will be referred to as the "second polymorph". Its melting or sublimation enthalpy, determined in a differential scanning calorimetry measurement at a heating rate of 10° C./minute, may be in a range of 30 J/g to 35 J/g.

It is most preferred that its X-ray powder diffractogram comprises one or more of the following reflexes (±0.2 in 2θ and recorded using CuK$_\alpha$ radiation; the relative intensity I(rel) is 100 at most):

TABLE 2

| X-ray powder diffractogram | | | |
|---|---|---|---|
| 2θ | I(rel) | 2θ | I(rel) |
| 6.0 | 36 | 12.1 | 43 |
| 13.1 | 100 | 29.8 | 24 |
| 13.6 | 53 |  |  |
| 15.3 | 89 |  |  |
| 16.5 | 76 |  |  |
| 22.4 | 26 |  |  |
| 22.6 | 28 |  |  |
| 24.1 | 66 |  |  |

In another particular embodiment of the hydrochloride salt according to the invention the X-ray powder diffractogram of the salt comprises one or more of the following reflexes (±0.2 in 2θ): 8.3, 16.1, 18.6, 20.9, 28.0, 29.9.

In the context of the present invention this polymorph will be referred to as the "third polymorph". It is most preferred that its X-ray powder diffractogram comprises one or more of the following reflexes (±0.2 in 2θ and recorded using CuK$_\alpha$ radiation; the relative intensity I(rel) is 100 at most):

TABLE 3

| X-ray powder diffractogram | | | |
|---|---|---|---|
| 2θ | I(rel) | 2θ | I(rel) |
| 8.3 | 21 | 6.7 | 21 |
| 16.1 | 100 | 9.3 | 74 |
| 18.6 | 25 | 10.4 | 29 |
| 20.9 | 26 | 11.5 | 58 |
| 28.0 | 28 | 11.8 | 69 |
| 29.9 | 21 | 20.0 | 36 |

The present invention is further directed to a method for the production of a crystalline, anhydrous hydrochloride salt of 4,5α-epoxy-3,14-dihydroxy-17-methylmorphinan-6-on of formula (I) according to one or more of claims 1-5, comprising the steps of:

providing a hydrate hydrochloride salt of 4,5α-epoxy-3,14-dihydroxy-17-methylmorphinan-6-on of formula (I); and heating to a temperature of ≥130° C. to ≤210° C.

It is preferred that the heating step takes place in such a way that the water that has been liberated from the hydrate starting material is removed and therefore cannot form hydrate systems again.

In one embodiment, the method according to the invention further comprises the step of grinding the hydrate hydrochloride salt of 4,5α-epoxy-3,14-dihydroxy-17-methylmorphinan-6-one of formula (I) prior to heating. It has been found that introducing shear stress by grinding greatly reduces the degree of crystallinity of the monohydrate salt.

In another embodiment of the method according to the invention the heating is conducted during a hot-melt extrusion process. This has the advantage that the method can be integrated into the production of tamper-resistant formulations of oxymorphone hydrochloride.

A further aspect of the present invention is a pharmaceutical composition comprising an effective amount of a crystalline, anhydrous hydrochloride salt of 4,5α-epoxy-3,14-dihydroxy-17-methylmorphinan-6-one of formula (I) according to the invention.

The quantity of the crystalline, anhydrous oxymorphone hydrochloride amounting to an effective amount of this substance depends substantially on the type of formulation and on the desired dosage during the period of administration. The quantity of the respective compounds to be administered to the patient may vary and is, for example, dependent on the weight or age of the patient and also on the manner of administration, on the indication and on the degree of severity of the illness. Preferably 0.005 mg/kg to 5000 mg/kg, particularly preferably 0.05 mg/kg to 500 mg/kg, quite particularly preferably 0.5 mg/kg to 100 mg/kg, still more preferably 2 mg/kg to 20 mg/kg of body weight of the patient of at least one such compound are administered.

Oral formulations may be solid formulations, for example tablets, capsules, pills and pastilles, but oral formulations may also be liquid formulations, for example solutions, suspensions, syrups or elixirs. Liquid and solid formulations also encompass the incorporation of the crystalline, anhydrous oxymorphone hydrochloride into solid or liquid foodstuffs. Furthermore, liquids also encompass solutions for parenteral applications, such as, for example, solutions for infusion or injection.

The crystalline, anhydrous oxymorphone hydrochlorides can be used directly as powders (micronized particles), granulates, suspensions or solutions, or they may be mixed with other pharmaceutically acceptable ingredients and components and then pulverized, in order then to fill the powders into capsules consisting of hard or soft gelatin, to press tablets, pills or pastilles, or in order to suspend or dissolve the powders in a carrier for the purpose of preparing suspensions, syrups or elixirs. Tablets, pills or pastilles can be provided with a coating after pressing.

Pharmaceutically acceptable ingredients and components for the various types of formulation are known as such. It may, for example, be a question of binding agents such as synthetic or natural polymers, medicinal carriers, lubricating agents, surfactants, sweetening agents and flavoring agents, coating agents, preserving agents, dyestuffs, thickening agents, ancillary agents, antimicrobial agents and carriers for the various types of formulation.

Examples of suitable binding agents include gum arabic, gum tragacanth, acacia gum and biodegradable polymers such as homopolyesters or copolyesters of dicarboxylic acids, alkylene diols, polyalkylene glycols and/or aliphatic hydroxycarboxylic acids; homopolyamides or copolyamides of dicarboxylic acids, alkylenediamines and/or aliphatic aminocarboxylic acids; corresponding polyester-polyamide copolymers, polyanhydrides, polyorthoesters, polyphosphazenes and polycarbonates. The biodegradable polymers may be linear, branched or crosslinked. Specific examples are polyglycolic acid, polylactic acid and poly-d,l-lactic/glycolic acid. Other examples of polymers are water-soluble polymers such as, for example, polyoxaalkylenes (polyoxyethylene, polyoxypropylene and mixed polymers thereof), polyacrylamides and hydroxyl-alkylated polyacrylamides, polymaleic acid and esters or amides thereof, polyacrylic acid and esters or amides thereof, polyvinyl alcohol and esters or ethers thereof, polyvinyl imidazole, polyvinyl pyrrolidone and natural polymers, such as chitosan, for example.

Examples of medicinal carriers include phosphates, such as dicalcium phosphate.

Examples of suitable lubricating agents include natural or synthetic oils, fats, waxes or fatty-acid salts such as magnesium stearate.

Surfactants (surface-active agents) may be anionic, cationic, amphoteric or neutral. Examples of useful surfactants include lecithin, phospholipids, octyl sulfate, decyl sulfate, dodecyl sulfate, tetradecyl sulfate, hexadecyl sulfate and octadecyl sulfate, sodium oleate or sodium caprate, 1-acylaminoethane-2-sulfonic acids such as 1-octanoylaminoethane-2-sulfonic acid, 1-decanoylaminoethane-2-sulfonic acid, 1-dodecanoylaminoethane-2-sulfonic acid, 1-tetradecanoylamino-ethane-2-sulfonic acid, 1-hexadecanoylaminoethane-2-sulfonic acid and 1-octadecanoylaminoethane-2-sulfonic acid, bile acids, salts and derivatives thereof, such as, for example, cholic acid, deoxycholic acid, taurocholic acid, taurodeoxycholic acid and sodium glycocholates, sodium caprate, sodium laurate, sodium oleate, sodium lauryl sulfate, sodium cetyl sulfate, sulfated castor oil, sodium dioctyl sulfosuccinate, cocamidopropyl betaine and lauryl betaine, fatty alcohols, cholesterols, glycerin monostearate or distearate, glycerin monooleate or dioleate, glycerin monopalmitate or dipalmitate and polyoxyethylene stearate.

Examples of suitable sweetening agents include sucrose, fructose, lactose and aspartame.

Examples of useful flavoring agents include peppermint, oil of wintergreen or fruit flavor such as cherry or orange flavor.

Examples of suitable coating agents include gelatins, waxes, shellac, sugars and biodegradable polymers.

Examples of preservation agents include methylparaben or propylparaben, sorbic acid, chlorobutanol and phenol.

Examples of ancillary agents include aromatic principles.

Examples of suitable thickening agents include synthetic polymers, fatty acids, fatty-acid salts, fatty-acid esters and fatty alcohols.

Examples of suitable liquid carriers include water, alcohols (ethanol, glycerol, propylene glycol, liquid polyethylene glycols), polytriazines and oils. Examples of solid carriers are talc, aluminas, microcrystalline cellulose, silicon dioxide, aluminium oxide and similar solid substances.

The composition according to the invention may also contain isotonic agents such as, for example, sugars, physiological buffers and sodium chloride.

The composition according to the invention may also be formulated as an effervescent tablet or effervescent powder which decomposes in an aqueous environment, thereby formulating solutions or suspensions for drinking.

A syrup or a elixir may contain the crystalline, anhydrous oxymorphone hydrochloride, a sugar such as sucrose or fructose by way of sweetening agent, a preserving agent (such as methylparaben), a dyestuff and a flavoring agent (such as flavoring substances).

The composition according to the invention may also be a formulation with delayed and/or controlled release of the active substance upon contact with body fluids of the gastrointestinal tract, in order to achieve a substantially constant and effective level of the active substance in the blood plasma. For this purpose the crystalline, anhydrous oxymorphone hydrochloride can be embedded in a polymer matrix of a biodegradable polymer, of a water-soluble polymer or of both types of polymers, optionally together with a suitable surfactant. In this context, 'embedding' may signify the incorporation of microparticles into the polymer matrix. Formulations with delayed and controlled release of active substance can also be obtained by encapsulation of dispersed microparticles or emulsified microdroplets with the aid of known techniques for coating dispersions and emulsions.

The crystalline, anhydrous oxymorphone hydrochloride can also be used together with at least one further pharmaceutical active substance for combination therapies. To this end, at least one further active substance may be additionally dispersed or dissolved in the composition according to the invention.

Yet another aspect of the present invention is a crystalline, anhydrous hydrochloride salt of 4,5α-epoxy-3,14-dihydroxy-17-methylmorphinan-6-one of formula (I) according to the invention as a medicament. With further reference to the detailed description above, the medicament to the invention may exist as a liquid, semisolid or solid medicinal form, for example in the form of injection solutions, drops, juices, syrups, sprays, suspensions, tablets, patches, capsules, plasters, suppositories, ointments, creams, lotions, gels, emulsions, aerosols, or in multiparticulate form, for example in the form of pellets or granulates, optionally pressed into tablets, filled in capsules or suspended in a liquid, and may also be administered as such.

In a preferred manner, the medicament according to the invention is suitable for the treatment and/or prevention and/or inhibition of pain, preferentially of acute pain, chronic pain, neuropathic pain or visceral pain.

Finally, the present invention is also directed to a crystalline, anhydrous hydrochloride salt of 4,5α-epoxy-3,14-dihydroxy-17-methylmorphinan-6-one of formula (I) according to the invention for the treatment and/or prevention of pain.

Examples for such pain to be treated and/or prevented are selected from the group consisting of acute pain, chronic pain, neuropathic pain and visceral pain; of migraine; depressions; neurodegenerative diseases, preferentially selected from the group consisting of Parkinson's disease, Alzheimer's disease, Huntington's disease and multiple sclerosis; cognitive illnesses, preferentially cognitive deficiency conditions, particularly preferably attention-deficit syndrome (ADS), panic attacks; epilepsy; coughing; urinary incontinence; diarrhea; pruritus; schizophrenia; cerebral ischemias; muscular spasms; cramps; food-intake disorders, preferentially selected from the group consisting of bulimia, cachexia, anorexia and obesity; abuse of alcohol and/or drugs (in particular, nicotine and/or cocaine) and/or medicaments; dependence on alcohol and/or drugs (in particular, nicotine and/or cocaine) and/or medicaments, preferentially for the prophylaxis and/or reduction of withdrawal symptoms in the case of dependence on alcohol and/or drugs (in particular, nicotine and/or cocaine) and/or medicaments; development of tolerance phenomena in relation to medicaments, particularly in relation to opioids; gastro-oesophageal reflux syndrome; for diuresis; for antinatriuresis; for influencing the cardiovascular system; for anxiolysis; for heightening wakefulness; for heightening libido, for modulating motor activity and for local anaesthesia.

In a particularly preferred manner, the crystalline, anhydrous oxymorphone hydrochloride salt according to the invention is suitable for the treatment and/or inhibition of pain, preferentially of acute pain, chronic pain, neuropathic pain or visceral pain; depressions; epilepsy; Parkinson's disease; abuse of alcohol and/or drugs (in particular, nicotine and/or cocaine) and/or medicaments; dependence on alcohol and/or drugs (in particular, nicotine and/or cocaine) and/or medicaments; preferentially for the prophylaxis and/or reduction of withdrawal symptoms in the case of dependence on alcohol and/or drugs (in particular, nicotine and/or cocaine) and/or medicaments; of the development of tolerance phenomena in relation to medicaments, in particular in relation to opioids, or for anxiolysis.

Lastly, the present invention also encompasses a method of treating pain in a subject in need thereof, said method comprising administering to said subject an analgesically effective amount of a crystalline anhydrous oxymorphone hydrochloride according to the invention.

BRIEF DESCRIPTION OF THE DRAWINGS

The present invention will be further described with reference to the following figures and examples without wishing to be limited in any way.

FIG. 1 shows an XRPD diagram of the reference material oxymorphone hydrochloride monohydrate FIG. 2 shows a DSC diagram of the reference material oxymorphone hydrochloride monohydrate FIG. 3 shows a TGA diagram of the reference material oxymorphone hydrochloride monohydrate FIG. 4 shows an XRPD diagram of a first polymorph of crystalline anhydrous oxymorphone hydrochloride

Figure 5:
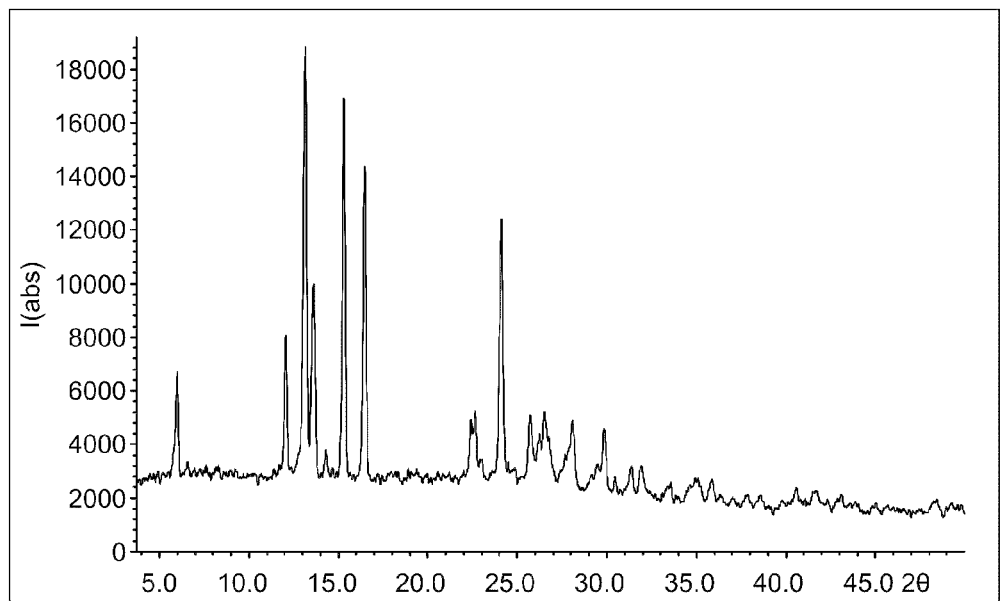
FIG. 5 shows an XRPD diagram of a second polymorph of crystalline anhydrous oxymorphone hydrochloride

Grinding experiments were carried out with a standard agate mortar at 20-25° C. and a relative humidity of 40-60%.

Humidity experiments were carried out at 20-24° C. by use of a saturated sodium chloride solution in an exsiccator, providing a relative humidity of approximately 70-75%.

DSC data were collected with a Mettler Toledo DSC821e/500 apparatus, Al standard pan (40 μl; with pinhole; N$_2$). Thermogravimetric data was obtained via a Mettler Toledo TGA/STDA module 851e.

Microscopic investigations were carried out with an Olympus BX51 microscope equipped with a Linkam TMS94 hot stage.

For the purpose of a better reference FIG. 1 shows an XRPD diagram of commercially supplied oxymorphone hydrochloride monohydrate. The DSC thermogram of this material is depicted in FIG. 2.

In this diagram two relevant thermal events can be observed. Starting at approximately 40° C. a broad endotherm is attributed to the loss of water, adhered water and the crystal water. The peak temperature of this endotherm was at 146° C.

The endotherm with an onset at 210° C. and a peak at 230° C. cannot be related to melting but to sublimation. This was confirmed by hot stage microscopy. The indication for sublimation is the broad endotherm and the comparatively low heat of only ca. 38 J/g. The sublimation is followed by degradation. Hot stage experiments with sublimation at over 200° C. only led to a degraded product. The sublimated materials were re-sublimated on a cold glass object plate. The resulting black solid was analyzed by GC-MS. The molar peak of oxymorphone was not found but rather only degradation products were detected.

The TGA data as represented in FIG. 3 show events that are comparable to those observed in the DSC experiment. The weight loss from 40-110° C. (onset temperature determined to be ca. 86° C.) represents the loss of water, 6.7% in total. Starting at ca. 210° C. the weight loss is attributed to sublimation/degradation.

FIG. 4 shows an XRPD diagram of a first polymorph of crystalline anhydrous oxymorphone hydrochloride. This material was produced by the following procedure: either crystalline oxymorphone hydrochloride or ground, mainly amorphous oxymorphone hydrochloride was heated to a temperature of 200° C. in a drying oven. The first polymorph was obtained as colorless, needle-type crystals growing on a solid form second polymorph (as described below). The crystals were separated manually and an X-ray powder diffraction pattern was determined. The XRPD peak list is given in the following table 4.

TABLE 4

| XRPD data | | |
|---|---|---|
| D | 2θ | I (rel) |
| 9.63 | 9.17 | 55 |
| 6.98 | 12.66 | 100 |

TABLE 4-continued

XRPD data

| D | 2θ | I (rel) |
|---|---|---|
| 6.39 | 13.83 | 18 |
| 6.01 | 14.71 | 52 |
| 5.78 | 15.31 | 38 |
| 5.75 | 15.38 | 38 |
| 5.45 | 16.23 | 28 |
| 5.16 | 17.14 | 25 |
| 4.88 | 18.16 | 12 |
| 4.79 | 18.47 | 13 |
| 4.65 | 19.04 | 24 |
| 4.60 | 19.25 | 16 |
| 4.45 | 19.92 | 53 |
| 4.31 | 20.55 | 30 |
| 4.09 | 21.71 | 22 |
| 3.85 | 23.06 | 13 |
| 3.81 | 23.32 | 14 |
| 3.65 | 24.36 | 21 |
| 3.61 | 24.59 | 42 |
| 3.57 | 24.89 | 16 |
| 3.50 | 25.40 | 13 |
| 3.48 | 25.54 | 13 |
| 3.36 | 26.49 | 16 |
| 3.19 | 27.87 | 16 |
| 3.09 | 28.81 | 18 |
| 2.99 | 29.76 | 11 |
| 2.95 | 30.21 | 13 |
| 2.87 | 31.11 | 11 |
| 2.80 | 31.85 | 29 |
| 2.68 | 33.35 | 15 |
| 2.58 | 34.63 | 19 |
| 2.46 | 36.42 | 10 |
| 2.32 | 38.69 | 9 |
| 2.13 | 42.24 | 9 |

After further heating of a mixture of the thus obtained first and second polymorphs the first polymorph disappeared. Possible explanations are sublimation (under degradation) or the transition onto the second polymorph.

FIG. 5 shows an XRPD diagram of the second polymorph of crystalline anhydrous oxymorphone hydrochloride. This polymorph was obtained by a heat treatment of either the above-described polymorph mixture or of oxymorphone hydrochloride monohydrate at 200° C. for a period of 3-4 hours in a drying oven. This form is stable at room temperature and at elevated temperatures and does not tend to transform into other polymorphs. The XRPD peak list is given in the following table 5.

TABLE 5

XRPD data

| D | 2θ | I (rel) |
|---|---|---|
| 14.72 | 5.99 | 36 |
| 7.32 | 12.06 | 43 |
| 6.72 | 13.14 | 100 |
| 6.50 | 13.60 | 53 |
| 6.18 | 14.30 | 20 |
| 5.78 | 15.30 | 89 |
| 5.37 | 16.47 | 76 |
| 3.96 | 22.41 | 26 |
| 3.92 | 22.64 | 28 |
| 3.68 | 24.09 | 66 |
| 3.46 | 25.71 | 26 |
| 3.39 | 26.24 | 23 |
| 3.35 | 26.50 | 27 |
| 3.17 | 28.06 | 25 |
| 2.99 | 29.84 | 24 |

TABLE 5-continued

XRPD data

| D | 2θ | I (rel) |
|---|---|---|
| 2.93 | 30.45 | 14 |
| 2.85 | 31.34 | 16 |
| 2.80 | 31.92 | 17 |

Figure 6:
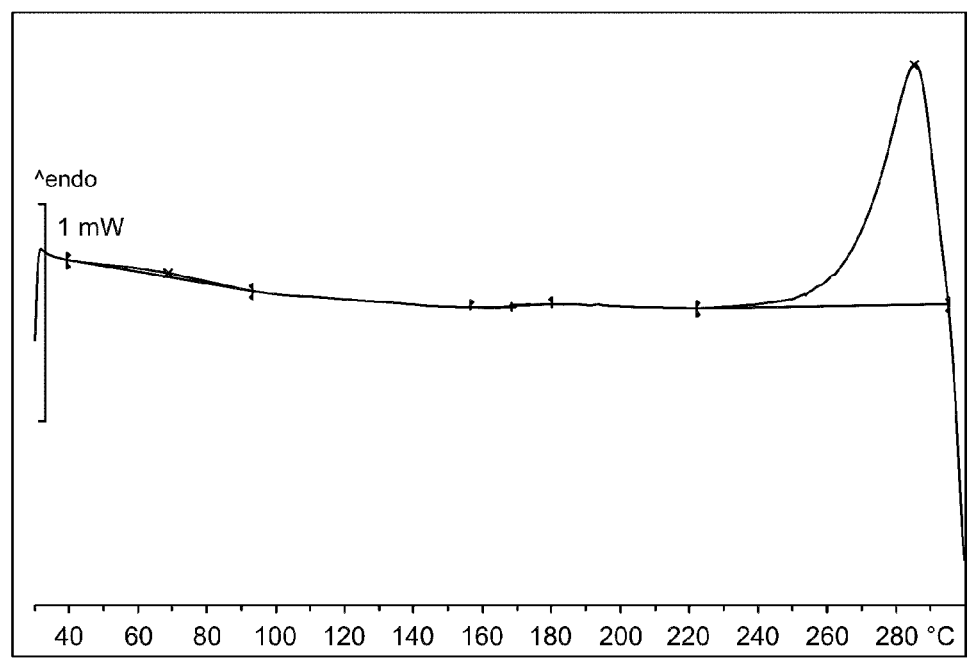
FIG. 6 shows a DSC diagram of the second polymorph of crystalline anhydrous oxymorphone hydrochloride

FIG. 6 shows a DSC diagram of the second polymorph. A first small endotherm is found with the following data: onset 39.43° C., peak 68.66° C. and a normalized integral of 0.78 J/g. A glass transition was found with an onset of 166.50° C. and a center point of 168.52° C. The strong endotherm has the following data: onset 266.91° C., peak 285.09° C. and a normalized integral of 33.16 J/g.

Figure 7:
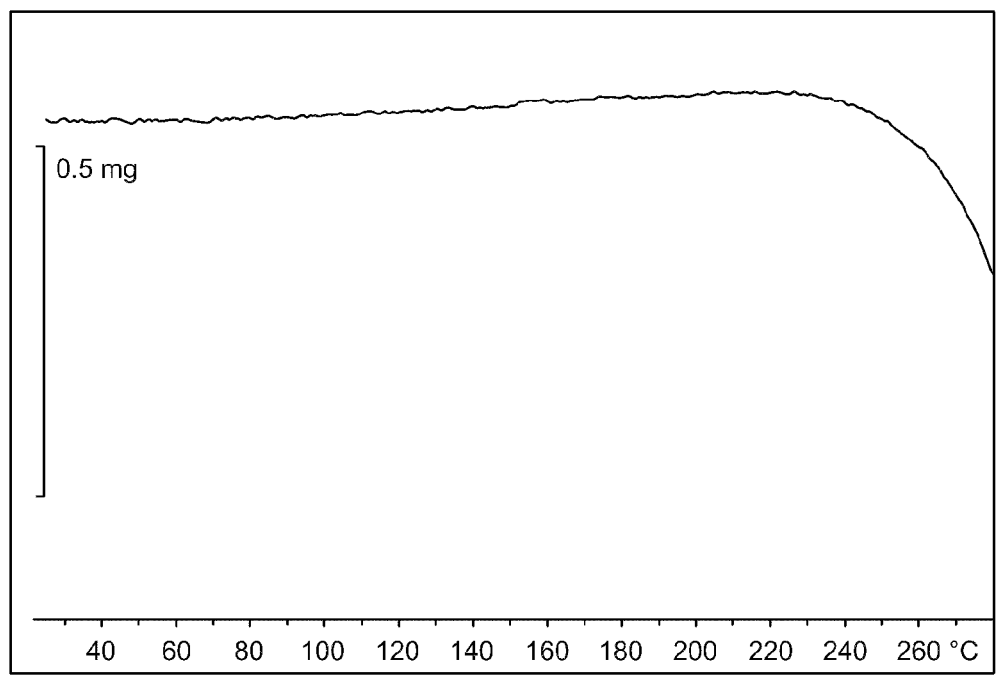
FIG. 7 shows a TGA diagram of the second polymorph of crystalline anhydrous oxymorphone hydrochloride

The TGA diagram in FIG. 7 displays no weight loss until a temperature of about 220° C. where according to the DSC measurements the sublimation process starts.

Figure 8:
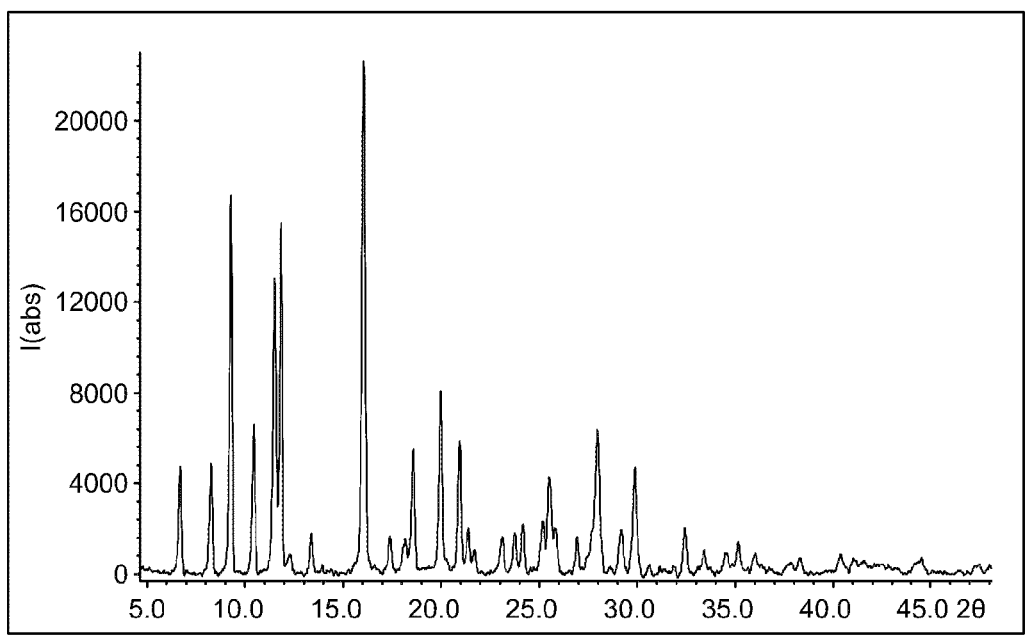
FIG. 8 shows an XRPD diagram of a third polymorph of crystalline anhydrous oxymorphone hydrochloride All powder diffraction patterns were determined with a STOE STADI P X-ray powder diffractometer, transmission geometry (Debye-Scherrer), CuK$_{\alpha 1}$ radiation, germanium monochromator, linear PSD, omega 2θ scan mode with a rotating flat sample. Variable temperature XRPD measurements were processed with the same diffractometer and geometry but using a capton foiled oven and a glass capillary. Detection of the diffracted pattern was undertaken with a STOE IPPSD. The data processing and analysis software used was Win XPOW® POWDAT.

A third polymorph of crystalline anhydrous oxymorphone hydrochloride was obtained in the circumstances of a variable temperature XRPD experiment, namely in the environment of the X-ray capillary used therein. The XRPD diagram of this third polymorph is shown in FIG. 8 and the XRPD peak list is given in the following table 6.

TABLE 6

XRPD data

| D | 2θ | I (rel) |
|---|---|---|
| 13.21 | 6.68 | 21 |
| 10.70 | 8.25 | 21 |
| 9.52 | 9.27 | 74 |
| 8.47 | 10.43 | 29 |
| 7.68 | 11.50 | 58 |
| 7.47 | 11.82 | 69 |
| 7.21 | 12.26 | 3 |
| 6.61 | 13.37 | 7 |
| 5.51 | 16.05 | 100 |
| 5.09 | 17.38 | 7 |
| 4.87 | 18.17 | 6 |
| 4.77 | 18.57 | 25 |
| 4.44 | 19.97 | 36 |
| 4.23 | 20.94 | 26 |
| 4.15 | 21.39 | 8 |
| 4.09 | 21.69 | 4 |
| 3.84 | 23.11 | 7 |
| 3.74 | 23.74 | 8 |
| 3.67 | 24.17 | 9 |
| 3.53 | 25.18 | 10 |
| 3.48 | 25.52 | 19 |
| 3.30 | 26.94 | 7 |
| 3.18 | 27.98 | 28 |
| 3.05 | 29.18 | 8 |
| 2.98 | 29.88 | 21 |
| 2.75 | 32.44 | 8 |
| 2.67 | 33.44 | 4 |
| 2.55 | 35.15 | 6 |

The invention claimed is:

1. A crystalline, anhydrous hydrochloride salt of 4,5α-epoxy-3,14-dihydroxy-17-methylmorphinan-6-one according to formula (I):

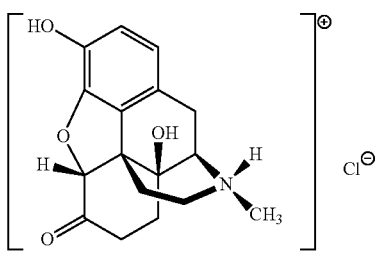

wherein the hydrochloride salt exhibits an X-ray powder diffractogram wherein peaks are observed at a grouping of peaks selected from the group consisting of A and B:
A) at (±0.2 in 2θ): 9.2, 12.7, 13.8, 14.7, 15.3, 16.2, 17.1, 19.0, 19.9, 20.6, 21.7, 24.6, 31.9 and 34.6; and
B) (±0.2 in 2θ): 6.0, 12.1, 13.1, 13.6, 15.3, 16.5, 22.4, 22.6, 24.1 and 29.8.

2. The hydrochloride salt according to claim 1, wherein the melting or sublimation temperature, defined as the peak temperature in a differential scanning calorimetry measurement at a heating rate of 10° C./minute, is ≥250° C.

3. A method for the preparation of a crystalline, anhydrous hydrochloride salt of 4,5α-epoxy-3,14-dihydroxy-17-methylmorphinan-6-one of formula (I) according to claim 1, comprising the steps of:
providing a hydrate hydrochloride salt of 4,5α-epoxy-3,14-dihydroxy-17-methylmorphinan-6-one of formula (I); and
heating to a temperature of ≥130° C. to ≤210° C.

4. The method according to claim 3, further comprising the step of grinding the hydrate hydrochloride salt of 4,5α-epoxy-3,14-dihydroxy-17-methylmorphinan-6-one of formula (I) prior to heating.

5. The method according to claim 3, wherein the heating is conducted during a hot-melt extrusion process.

6. A pharmaceutical composition comprising an effective amount of a crystalline, anhydrous hydrochloride salt of 4,5α-epoxy-3,14-dihydroxy-17-methylmorphinan-6-one of formula (I) according to claim 1.

7. A method of treating and/or inhibiting pain in a patient in need of such treatment, said method comprising administering to said patient an effective amount therefor of a crystalline, anhydrous hydrochloride salt of 4,5α-epoxy-3,14-dihydroxy-17-methylmorphinan-6-one of formula (I) according to claim 1.

8. The pharmaceutical composition of claim 6, wherein the effective amount of a crystalline, anhydrous hydrochloride salt of 4,5α-epoxy-3,14-dihydroxy-17-methylmorphinan-6-one is from about 0.05 mg/kg to about 500 mg/kg of body weight of a patient.

9. The pharmaceutical composition of claim 6, wherein the composition is a delayed release composition.

10. The pharmaceutical composition of claim 6, wherein the composition is a controlled release composition.

11. The pharmaceutical composition of claim 6, wherein the composition is used with at least one other pharmaceutical active substance.

12. A method of treating pain in a subject in need thereof, said method comprising administering to said subject an analgesically effective amount of the crystalline, anhydrous hydrochloride salt of 4,5α-epoxy-3,14-dihydroxy-17-methylmorphinan-6-one of formula (I) according to claim 1.

13. The hydrochloride salt according to claim 1, wherein the melting or sublimation temperature, defined as the peak temperature in a differential scanning calorimetry measurement at a heating rate of 10° C./minute, is from about 280° C. to about 290° C.

* * * * *